United States Patent [19]
Haze et al.

[11] Patent Number: 5,919,662
[45] Date of Patent: Jul. 6, 1999

[54] MICROORGANISM HAVING LOW ACETATE FORMING CAPABILITY, AND PROCESS FOR PRODUCTION OF USEFUL SUBSTRATE USING SAME

[75] Inventors: Shinichiro Haze; Ohji Ifuku; Jiro Kishimoto, all of Yokohama, Japan

[73] Assignee: Shiseido Company, Ltd., Tokyo, Japan

[21] Appl. No.: 08/970,092

[22] Filed: Nov. 13, 1997

Related U.S. Application Data

[62] Continuation of application No. 08/643,979, May 7, 1996, abandoned, which is a continuation of application No. 07/381,413, filed as application No. PCT/JP88/01124, Nov. 7, 1987, abandoned.

[30] Foreign Application Priority Data

Nov. 7, 1987 [JP] Japan .................................. 62-281826

[51] Int. Cl.$^6$ ................................ C12P 1/04; C12N 1/21; A61K 31/415
[52] U.S. Cl. .................. 435/69.1; 435/71.2; 435/252.33; 514/387
[58] Field of Search .................................. 435/69.1, 71.2, 435/252.33; 514/387

[56] References Cited

FOREIGN PATENT DOCUMENTS

| 0219791 | 4/1987 | European Pat. Off. . |
| 61-202686 | 9/1986 | Japan . |
| 62-155081 | 10/1987 | Japan . |

OTHER PUBLICATIONS

Kane et al., TIBTECH, vol. 6, pp 95–101 (1986).
Ivanov et al., FEBS Lett., 210 (1), pp 56–60 (1987).
Pascal et al., J. Gen. Microbiol., 124 pp. 35–42 (1981).
Guest., J. of Gen. Microbiol., 115, pp. 259–271 (1979).
Brown et al., J. Gen. Micro., vol. 102 pp 327–336 (1977).
LeVine et al., J. Bact., vol. 143 No. 2, pp. 1081–1085 (1980).
Rehm, in Biotechnology, Verlagesellschatt, Weinheim, pp. 144–150 (1986).
Allen et al. Biopharm., pp. 38–41, Nov. 1987.
Suzuki, Biochim. Biophys. Acta, vol. 191, pp. 559–569 (1969).
Jung et al., Ann. Inst. Pasteur/Micro., vol. 139, pp 129–146 (1988).
Iijima, et al., Appl. Microbiol. Biotech. vol. 26, pp. 542–545 (1987).
Zabriskie et al., Enzyme Microb. Technol. vol. 8, pp 706–777 (1986).
Stephen Harford et al., FEBS LETTER vol. 114, No. 2, 339–341, 1980.
Judith E. Miller et al., J. Ind. Microbiology 2, 143–149, 1987.

Primary Examiner—Johnny F. Railey, II
Attorney, Agent, or Firm—Foley & Lardner

[57] ABSTRACT

*Escherichia coli* characterized in that a capability thereof of forming acetate is at most one fifth that of wild type *Escherichia coli*, and a process for producing a useful substance by cultivating the *Escherichia coli* to a high density and recovering the substance

5 Claims, 1 Drawing Sheet

MICROORGANISM HAVING LOW ACETATE FORMING CAPABILITY, AND PROCESS FOR PRODUCTION OF USEFUL SUBSTRATE USING SAME

This application is a continuation of application Ser. No. 08/643,979, filed May 7, 1996, now abandoned, which is a continuation of application Ser. No. 07/381,413, filed Jul. 3, 1989, now abandoned, which is a national stage application filed under 35 U.S.C. § 371 of PCT/JP88/01124, filed Nov. 7, 1987.

TECHNICAL FIELD

The present invention relates to a novel microorganism, particularly *Escherichia coli*, having a low acetate forming capability in comparison with the capability of a wild type *Escherichia coli*, and a process for producing a useful substance with a good yield by cultivating the microorganism in a high density The term "acetate forming capability", "capability of forming acetate" or the like used herein means an amount of accumulated acetate on the basis of bacterial dry weight, when cultivating *Escherichia coli* under adequate cultivating conditions.

BACKGROUND ART

A chemical synthesis of useful substances such as a protein or vitamin requires complicated processes, and thus is expensive. Therefore, efficient processes for producing such substances by fermentation methods using microorganisms have been developed.

Biotin is a vitamin, essential for animals, plants and microorganisms, and can be used as an additive for a feed or a liquid for transfusion, or the like. The development of such fermentation methods for biotin has been attempted, and Japanese Unexamined Patent Publication (Kokai) No. 61-202686 and No. 62-155081, and WO87/01391 disclose processes for preparing biotin using strains of *Escherichia coli* improved by a genetic engineering technique.

Generally speaking, when the substance is produced using a microorganism, it is an effective means of achieving a high density of the microorganism in a culture broth with a fed-batch culture or the like, in view of not only an increased yield of the product but also an efficient employment of a fermenter and an efficient recovery of the product. In the case of *Escherichia coli*, many advantages could be obtained from the high density cultivation, particularly of *Escherichia coli* improved by a genetic engineering technique. But, in the case of *Escherichia coli*, acetate is formed with a metabolism of nutrients, and accumulated in a considerable amount in the culture broth, thereby inhibiting an activity of growth of the cell, and therefore, the realization of a high density cultivation was difficult. As the means of solving the above problem and achieving a high density cultivation, a dialysis or filtration cultivating method is known wherein the formed acetate is removed from the cultivation system by dialysis or filtration of the culture broth.

Further, a pressurized culture was proposed wherein a pure oxygen gas is used to maintain a high concentration of a dissolved oxygen in the culture broth, thereby suppressing the amount of acetate formed (Matsui, et al, Synopses of Presentations on Convention in 1986, Fermentation Engineering Association of Japan, p. 206).

Nevertheless, problems arise in the dialysis or filtration culture, for example, the necessity for exclusive use equipment or a complicated maintenance of the equipment, and thus this is not economical or practical. Further, some useful substances (e.g., biotin) produced by *Escherichia coli* and accumulated can be dialyzed or filtrated from the culture broth together with acetate and therefore, it is necessary in the recovery step of the useful substances to deal with a large amount of the liquid containing a low concentration of the substances, and thus the advantage gained by carrying out the high density cultivation is almost completely lost. The high density cultivation of *Escherichia coli* with the pressurized culture brings a complicated control during cultivation operations or conditions, and is not easily achieved.

DISCLOSURE OF THE INVENTION

After conducting various research projects to remedy the above-mentioned problems from a viewpoint different from that of the prior art, i.e., from the viewpoint of the genetic improvement of *Escherichia coli*, the present inventors successfully achieved an artificial mutation of strains of wild type *Escherichia coli* to obtain mutant strains exhibiting a low acetate synthetic capability, which capability is one fifth or less than that of the wild type. The inventors found that, when the mutant strains are used in the production of the useful substances, a high density cultivation can be easily achieved without encountering the inhibition of the growth activity with the acetate formed, even if special culture methods, such as a dialysis, filtration or pressurized culture method are not employed. Further, the inventors found that these mutant strains can be transformed with a recombinant plasmid having genetic information relating to a production of a useful substance. For example, when the recombinant plasmid containing a biotin operon is introduced to the mutant strain and the resulting strain is cultured, not only do the cells of the strain reach a high density without an inhibition of the growth activity with the acetate, but also the growth activity is maintained, and thus an intermediate metabolite, desthiobiotin, is efficiently metabolized to biotin and the yield of biotin is greatly increased, whereas desthiobiotin was retained and accumulated in the culture broth as the intermediate of a biosynthesis of biotin in the conventional cultivation methods. Furthermore, the inventors found that the yield of desthiobiotin and biotin produced is considerably increased by adding a predetermined amount of alanine to the culture broth.

Accordingly, the present invention relates to *Escherichia coli* characterized in that the capability thereof of forming acetate is at most one fifth that of the wild type *Escherichia coli*.

Further, the present invention also relates to *Escherichia coli* having a capability of forming acetate of at most one fifth that of wild type *Escherichia coli*, and which contains a recombinant plasmid having genetic information relating to the production of the useful substance.

Furthermore, the present invention relates to a process for producing a useful substance, characterized by cultivating, in a high density, *Escherichia coli* having a capability of forming acetate of at most one fifth that of wild type *Escherichia coli*, and which contains a recombinant plasmid having genetic information relating to the production of the useful substance; and recovering the useful substance produced.

BEST MODE FOR CARRYING OUT THE INVENTION

Figure 1:
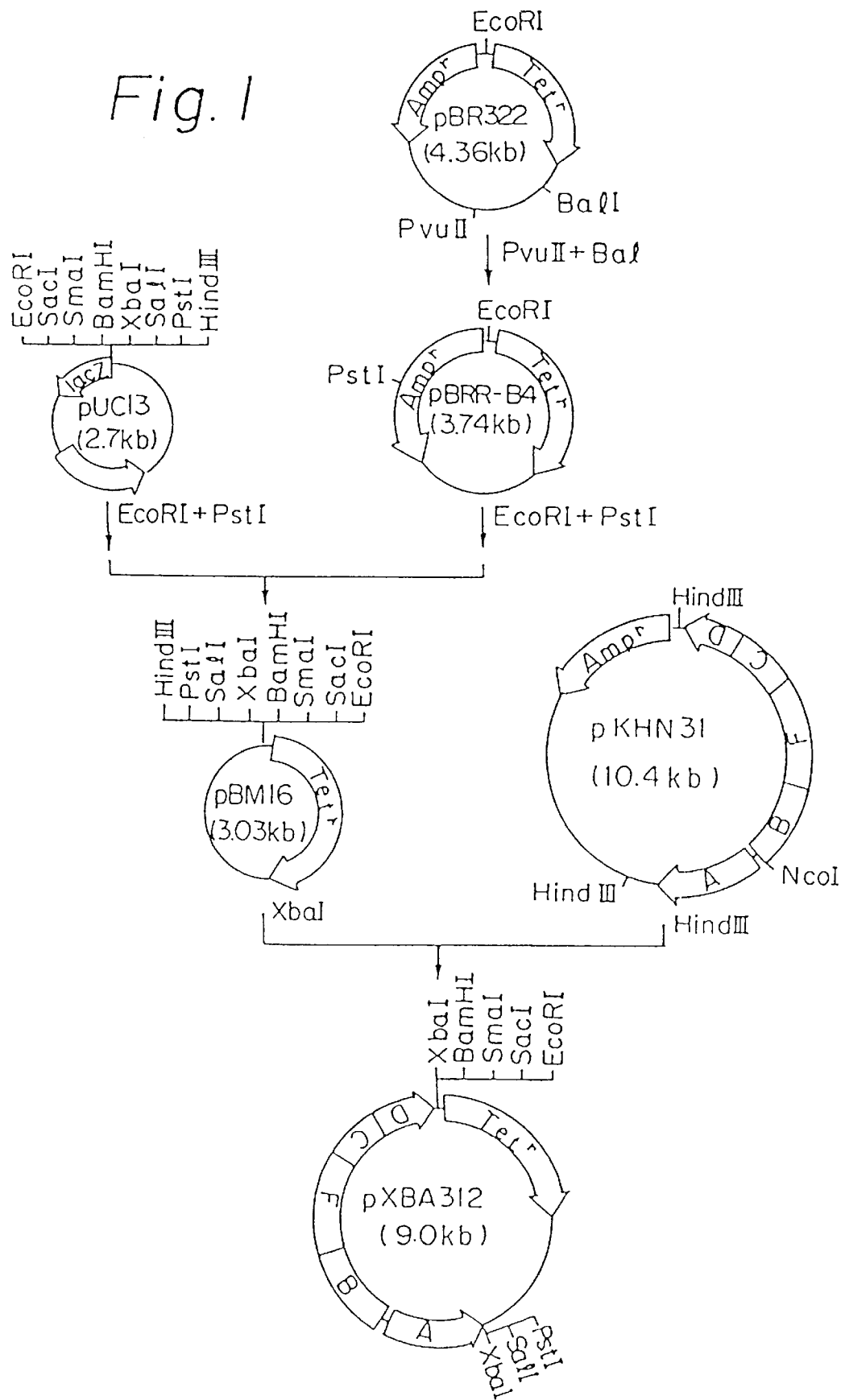
FIG. 1 illustrates a process for preparing plasmid pXBA 312 as explained in Example 3.

Preparation of Microorganisms of the Present Invention

The strain (hereinafter referred to as AD mutant strain) of *Escherichia coli* having a capability of forming acetate of at most one fifth that of the wild type may be obtained by subjecting the strain of wild type *Escherichia coli* to a conventional mutagenic treatment; cultivating under shaking the resulting bacterial cells in an appropriate culture broth; determining concentrations of the bacterial cells and the amount of acetate accumulated in the medium; and selecting the AD mutant strains having a capability of forming acetate that is at most one fifth of that of the wild type strain. In a preferred embodiment; mutant strains of *Escherichia coli* exhibiting a resistance to sodium fluoroacetate (hereinafter referred to as FR mutant strain) are first selected from among the bacterial cells obtained through a mutagenic treatment and then, from among FR mutant strains, the strains having a lower acetate forming capability than that of the wild type are selected. This is because in many cases, *Escherichia coli* having a low acetate forming capability can be found in FR mutant strains.

More particularly, wild type *Escherichia coli* is first subjected to a conventional mutagenic treatment, for example, to a treatment with a mutagenic agent such as N-methyl-N'-nitro-N-nitrosoguanidine, the resulting cells are appropriately diluted with a buffer and cultivated on a minimum agar plate containing proline as a sole carbon source and sodium fluoroacetate, and then the resulting colonies are separated into individual FR mutant strains. The separated FR mutant strains are then cultivated under shaking in appropriate liquid media, the amount of acetate accumulated in each medium is determined through liquid chromatography or an assay kit using enzymatic reactions (F Kit: Boehringer Mannheim Yamanouchi) or the like, and then the AD mutant strains having a capability of forming acetate that is at most one fifth of that of the wild type strain are selected and harvested. The resulting strains have a low acetate forming capability and a resistance to sodium fluoroacetate. When the cultivation is carried out in a conventional medium in such a manner that the dissolved oxygen is not allowed to become insufficient, the amount of the accumulated acetate per bacterial dry weight in the medium is generally 0.5–1.5 for the wild type strains, and 0.1 or less for the AD mutant strains according to the present invention. The amount of the accumulated acetate per bacterial dry weight is a quotient from a division of the amount of the accumulated acetate (g/l) by the cell concentration (g/l).

Instead of the strains of wild type *Escherichia coli*, strains of *Escherichia coli* wherein a feedback repression by biotin is removed (hereinafter referred to as DR mutant strain), such as *Escherichia coli* DRK-332 [FERM BP-2113; all the numbers cited herein as "FERM BP" refer to the deposition numbers of the Fermentation Research Institute (FRI) as the international depository authority under Budapest Treaty: internally transferred from FERM P-8585 originally deposited in the FRI as the domestic depository authority in Japan; all the numbers cited herein as "FERM P" refer to the deposition numbers of the FRI as the domestic depository authority] can be used as a parent strain for the same mutagenic treatment to obtain a mutant strain having a low acetate forming capability, and a resistance to sodium fluoroacetate, and wherein the feedback repression by biotin is removed. As the AD mutant strain obtained as above, there may be enumerated *Escherichia coli* DRK-3323 (FERM BP-2116: FERM P-9675). A recombinant plasmid prepared by inserting a biotin operon isolated from a biotin-producing *Escherichia coli* into a vector DNA can be obtained in accordance with the process disclosed in Japanese Unexamined Patent Publication (Kokai) No. 62-155081, and includes, for example, plasmid pKHN31. Further, a phenotype of the vector in such a recombinant plasmid can be rendered resistant to tetracycline, to obtain a stable recombinant plasmid which is not eliminated during a subsequent high density cultivation.

Alternatively, the AD mutant strain containing the recombinant plasmid can be obtained by introducing the recombinant plasmid obtained as above into the AD mutant strain (e.g., *Escherichia coli* DRK-3323) by a conventional method, such as a calcium chloride procedure disclosed in Mandel M., et al, J. Mol. Biol., 53, 109 (1970); cultivating the resulting transformant on an agar medium plate in which the clones of the bacterial cells containing the recombinant plasmid can be selectively grown, due to the phenotype of the vector therein; and then separating the colonies.

The AD mutant strains containing the resulting recombinant plasmid include, for example, *Escherichia coli* DRK-3323 [pXBA3121] (FERM BP-2117: FERM P-9676).

When a human calcitonin (hereinafter referred to as hCT) is desired as the useful substance, AD mutant strains containing the corresponding recombinant plasmid may be prepared. For example, plasmid pZT 32 may be isolated from *Escherichia coli* M15 [pZT 32] (FERM BP-2115: FERM P-9266) which contains the recombinant plasmid having genes coding a fusion protein (hCT-peptide containing collagenase cleavage site-β-galactosidase) and tac-promoter, and introduced into the AD mutant strains such as *Escherichia coli* NA-75 (FERM BP-2105) to obtain *Escherichia coli* NA-75 [pZT 32].

If other useful substances are desired, a recombinant DNA can be prepared from a gene relating to a production of the desired substance and a vector DNA, and introduced into the AD mutant strain to obtain a desired microorganism.

High Density Cultivation

The *Escherichia coli* prepared as above according to the present invention can be easily cultivated to a high density without encountering an inhibition of the growth activity by acetate.

As the culture medium for cultivating the *Escherichia coli* according to the present invention, a synthetic medium containing a carbon source, nitrogen source and/or inorganic substances, or a natural medium, may be used. The carbon source which may be used includes carbohydrate such as glucose, glycerol, fructose, sucrose, maltose, starch, hydrolyzed starch liquor, molasses, or the like. The nitrogen source which may be used includes ammonia, various inorganic or organic ammonium salts such as ammonium chloride, ammonium phosphate, ammonium sulfate or the like, or a natural organic nitrogen source such as amino acid, meat extract, yeast extract, corn-steep liquor, casein hydrolysate, defatted soybean or digest thereof, or the like. Many natural nitrogen sources may include not only the nitrogen source but also the carbon source. As the inorganic substances, dipotassium hydrogenphosphate, potassium dihydrogenphosphate, magnesium sulfate, sodium chloride, ferrous sulfate, calcium chloride, zinc chloride, copper sulfate, manganese chloride, cobalt chloride, ammon molybdate, boric acid, or the like may be used.

When an antibiotic resistance gene is included with the prepared microorganism, contamination may be prevented by adding the corresponding antibiotic into the medium.

The above nutrients may be added all at once to the medium in the total amounts thereof necessary for the cultivation, before the beginning of the cultivation. Some nutrients cause the reduction of the growth activity or the like of the *Escherichia coli*, if added all at once in the total necessary amounts. When using such nutrients, it is preferable to add a part of the nutrients into the medium at the beginning of the cultivation, and then feed the remainder in an amount corresponding to the consumption by the growth, during the course of the cultivation.

When biotin is produced using the microorganism according to the present invention, the yield thereof can be increased by adding alanine to the medium. The alanine used may be D-compound, L-compound or DL-compound, each of which brings similar effects. The DL-compound is preferable in view of the cost. The concentration of alanine added to the medium is preferably 1–10 g/l, more preferably 3–7 g/l. If the concentration exceeds 10 g/l, alanine causes the inhibition of the growth of the cells, particularly the reduction of the productivity of biotin. Alanine may be added all at once at the beginning of the cultivation, or in portions during the cultivation.

The microorganism according to the present invention exhibits a low acetate forming capability independently of the influence of the aeration and agitation conditions. Therefore, it is not necessary to maintain the high concentration of the dissolved oxygen in the medium, to suppress the accumulation of acetate, as in the prior art. Nevertheless, it is preferable to maintain the concentration of the dissolved oxygen at 3–6 ppm to efficiently metabolize the nutrients. Preferably, the cultivation temperature is 25°–38° C., and preferably the pH during the cultivation is maintained as substantially neutral. A cultivation time of about 16–48 hours is usually sufficient, and at the end of the cultivation, the concentration of the cells has a dry weight of 50 g/l or more.

Production of Biotin

A considerable amount of biotin can be produced and accumulated in the culture broth by cultivating, to a high density as above, the present *Escherichia coli* containing the recombinant plasmid prepared by inserting the biotin operon into the vector DNA. After the cultivation is completed, biotin can be extracted and purified from the culture broth, using the properties of biotin, by employing extraction-purification methods analogous to those for extracting and purifying a substance from natural materials. After the bacterial cells are removed from the culture broth, biotin can be adsorbed on an activated carbon, then eluted and purified by an ion exchange resin. Alternatively, biotin can be purified by treating a filtrate of the culture directly with the ion exchange resin. After recrystallization from water or alcohol, a purified biotin can be obtained.

EXAMPLES

The present invention now will be further illustrated by, but is by no means limited to, the following Examples.

Example 1

Preparation of AD Mutant Strain

*Escherichia coli* W3110 strain (IFO 12713) was cultivated under shaking at 37° C. for 3 hours in an L-medium (10 g/l of peptone, 5 g/l of yeast extract, 1 g/l of glucose, 5 g/l of sodium chloride; adjusted to pH 7.2). Bacterial cells in a logarithmic growth phase were harvested, washed, and then suspended in a TM buffer (0.61% of tris-base, 0.5% of maleic acid; adjusted to pH 6.0) containing 100 µg/ml of N-methyl-N'-nitro-N-nitrosoguanidine, and allowed to stand at 37° C. for 30 minutes for mutagenesis. After harvesting and washing, the cells were put in the L-medium to carry out a restorative cultivation at 37° C. for 3 hours. The cells were harvested, washed, and then suspended in sterilized water to about $10^7$ cells/ml. The suspension was spread on a proline minimum agar plate (1 g/l of proline, 4 g/l of ammonium sulfate, 2 g/l of potassium dihydrogenphosphate, 1 g/l of dipotassium hydrogenphosphate, 0.1 g/l of magnesium sulfate.$7H_2O$, 5 g/l of sodium chloride, 15 g/l of agar) containing 5 g/l of sodium fluoroacetate in an amount of 0.1 ml/Petri dish, and the cultivation was carried out at 37° C. for 48 hours. The emerged colonies were separated into individual FR mutant strains. Due to the difference in the mechanisms of obtaining the resistance, the FR mutant strains include the AD mutant strains having a reduced capability of forming acetate in comparison with the parent strain, and the strains which have an unchanged acetate forming capability.

To compare the acetate forming capabilities of the isolated FR mutant strains and the parent strain W 3110, the cells were cultivated under shaking at 37° C. for 24 hours in a 500 ml Sakaguchi flask containing 50 ml of a medium for a test of the capability of forming acetate (5 g/l of ammonium sulfate, 13.2 g/l of sodium dihydrogenphosphate-$12H_2O$, 1.8 g/l of dipotassium hydrogenphosphate, 1 g/l of magnesium sulfate.$7H_2O$, 10 g/l of peptone, 10 g/l of yeast extract, 10 g/l of glucose). The shaking rate was 120 strokes/minute. After the cultivation was completed, an optical density at the wavelength of 660 nm ($OD_{660}$) was measured for each culture broth with a spectrophotometer, and then converted to the cell concentration (g/l) on the basis of a standard curve which had been prepared between the dry cell weight and $OD_{660}$. The cells were then centrifuged, and the amount of acetate in the supernatant of each culture broth was determined with a quantitative analysis kit using enzymatic reactions (F Kit; Boeringer Manheim Yamanouchi). An AD mutant strain NA-75 (FERM BP-2105) was obtained having a capability of forming acetate of less than one fifth of that of the parent strain The results of the comparison in the acetate forming capability between the parent strain W3110 and AD mutant strain NA-75 are shown in Table 1.

TABLE 1

| Strain | Cell concentration (g/l) | Amount of accumulated acetate (g/l) | Amount of accumulated acetate per bacterial dry weight |
|---|---|---|---|
| Parent strain | | | |
| *Escherichia coli* W3110 (IFO12713) | 5.1 | 4.5 | 0.88 |
| AD mutant strain | | | |
| *Escherichia coli* NA-75 (FERM BP-2105) | 4.5 | 0.4 | 0.09 |

Example 2

Preparation of AD Mutant Strain from *Escherichia coli* Wherein Feedback Repression by Biotin is Removed

*Escherichia coli* DRK-332 (FERM BP-2113) wherein the feedback repression by biotin is removed was cultivated under shaking at 37° C. for 3 hours in an L-medium (10 g/l of peptone, 5 g/l of yeast extract, 1 g/l of glucose, 5 g/l of sodium chloride; adjusted to pH 7.2). Bacterial cells in a logarithmic growth phase were harvested, washed, and then suspended in a TM buffer (0.61% of tris-base, 0.5% of maleic acid; adjusted to pH 6.0) containing 100 μg/ml of N-methyl-N'-nitro-N-nitrosoguanidine, and allowed to stand at 37° C. for 30 minutes for mutagenesis. After harvesting and washing, the cells were put in an L-medium to carry out a restorative cultivation at 37° C. for 3 hours. The cells were harvested, washed, and then suspended in sterilized water to about $10^7$ cells/ml. The suspension was spread on a proline minimum agar plate (1 g/l of proline, 4 g/l of ammonium sulfate, 2 g/l of potassium dihydrogenphosphate, 1 g/l of dipotassium hydrogenphosphate, 0.1 g/l of magnesium sulfate.7H$_2$O, 5 g/l of sodium chloride, 15 g/l of agar) containing 5 g/l of sodium fluoroacetate in an amount of 0.1 ml/Petri dish, and the cultivation was carried out at 37° C. for 48 hours. The emerged colonies were separated into individual FR mutant strains. Due to the difference in mechanisms of obtaining the resistance, the FR mutant strains include the AD mutant strains which have a reduced acetate forming capability in comparison with the parent strain, and the strains which have an unchanged acetate forming capability.

To compare the acetate forming capabilities of the isolated FR mutant strains and the parent strain DRK-332, the cells were cultivated under shaking at 37° C. for 24 hours in a 500 ml Sakaguchi flask containing 10 ml or 100 ml of a medium for a test of the capability thereof of forming acetate (5 g/l of ammonium sulfate, 13.2 g/l of sodium dihydrogenphosphate-12H$_2$O, 1–8 g/l of dipotassium hydrogenphosphate, 1 g/l of magnesium sulfate.7H$_2$O, 10 g/l of peptone, 10 g/l of yeast extract, 10 g/l of glucose). The shaking rate was 120 strokes/minutes. Aeration conditions were varied by taking two levels of medium amount (10 ml or 100 ml). After the cultivation was completed, an optical density at the wavelength of 660 nm (OD$_{660}$) was measured for each culture broth with a spectrophotometer and then converted to the cell concentration (g/l) on the basis of a standard curve which had been prepared between dry cell weight and OD$_{660}$. The cells were then centrifuged, and the amount of acetate in the supernatant of each culture broth was determined with a quantitative analysis kit using enzymatic reactions (F Kit; Boeringer Mannheim Yamanouchi). An AD mutant strain DRK-3323 (FERM BP-2116) was obtained having a capability of forming acetate of less than one fifth of that of the parent strain. The results of the comparison in the acetate forming capability between the parent strain DRK-332 and AD mutant strain DRK-3323 are shown in Table 2. It is apparent from Table 2 that the AD mutant strain DRK-3323 was not affected by the aeration conditions, and the amount of accumulated acetate per bacterial dry weight was less than 0.25 even under the poor aeration condition wherein insufficient dissolved oxygen was present.

TABLE 2

| Strain | | Parent strain Escherichia coli DRK-332 (FERM BP-2113) | AD mutant strain Escherichia coli DRK-3323 (FERM BP-2116) |
| --- | --- | --- | --- |
| Cultivation | Cell conc. (g/l) | 2.0 | 2.5 |
| under low aeration *1 | Amount of accumulated acetate (g/l) | 4.5 | 0.6 |
| | Amount of accumulated acetate per bacterial dry weight | 2.25 | 0.24 |
| Cultivation under high aeration *2 | Cell conc. (g/l) | 2.2 | 5.8 |
| | Amount of accumulated acetate (g/l) | 3.3 | 0.5 |
| | Amount of accumulated acetate per bacterial dry weight | 1.50 | 0.09 |

*1: 100 ml of medium was charged into 500 ml flask.
*2: 10 ml of medium was charged into 500 ml flask.

Example 3

Preparation of AD Mutant Strain Containing Recombinant Plasmid Having Biotin Operon (1) Preparation of vector DNA A strain of *Escherichia coli* K-12 containing plasmid pBR 322 (Peden, K., Gene, 22, 277, 1983) was cultivated under shaking at 37° C. for a day in an LB medium [1% of Bacto tryptone (manufactured by Difco), 0.5% of Bacto yeast extract (manufactured by Difco), 1% of sodium chloride; adjusted to pH 7.2 with sodium hydroxide] to obtain cells, and then plasmid DNA pBR322 was taken by the alkaline lysis method (Birnboim, H. C. et al, Nucl. Acid Res., 7, 1513, 1979)

As illustrated in FIG. 1, the resulting plasmid DNA pBR322 (1 μg) was cleaved with two restriction endonucleases Pvu II and Bal I, treated by electrophoresis through 1% low-gelling temperature agarose gel (Type VII manufactured by Sigma), and then stained with ethidium bromide. A DNA fragment (about 3.7 kb) was cut off, and heated at 70° C. for 5 minutes. An almost identical amount of phenol saturated with a TE buffer (10 mM tris hydrochloride buffer, pH 8.0, 1 mM EDTA) was added thereto, and the whole was thoroughly mixed and centrifuged to obtain an aqueous phase. To the aqueous phase, two volumes of ethanol were added, and precipitated vector DNA fragment was ligated with a DNA ligation kit (manufactured by Takara Shuzo).

*Escherichia coli* M15 (Δ [lac-Pro], thi, φ80d, lacZM15, ara, rpsl, recA,) [obtained from Pharmacia] was transformed with the resulting recombinant DNA solution. The transformation was carried out by calcium chloride procedure. By growing on a plate of an LB medium [1% of Bacto tryptone (manufactured by Difco), 0.5% of Bacto yeast extract (manufactured by Difco), 1% of sodium chloride, 1.5% of agar; adjusted to pH 7.2 with sodium hydroxide] containing 50 μg/ml ampicillin, transformed strain *Escherichia coli* M15 [pBRR-B4] was obtained.

*Escherichia coli* M15 [pBRR-B4] was cultivated on an LB medium containing 50 μg/ml of ampicillin, and plasmid pBRR-B4 was taken by the above-mentioned alkaline lysis method.

The resulting plasmid pBRR-B4 (1 μg) was cleaved with two restriction endonucleases Eco RI and Pst I, and treated by 1% agarose electrophoresis through low-gelling temperature agarose. Thus, a DNA fragment (about 3.0 kb.) was isolated and taken as mentioned above.

On the other hand, a plasmid DNA pUC 13 (obtained from Pharmacia) (2 μg) was cleaved with two restriction endonucleases Eco R1 and Pst I, treated by electrophoresis through 15% polyacrylamide gel (manufactured by Nakarai) and then stained with ethidium bromide. A DNA fragment (about 40 b) was cut off and homogenized in a Dounce homogenizer (manufactured by Wheaton Scientific) with 0.5M ammonium acetate (containing 1 mM EDTA) and the identical amount of phenol solution saturated with a TE buffer, and the whole was thoroughly mixed and centrifuged to obtain an aqueous phase. To the aqueous phase, two volumes of ethanol were added, and after centrifuging, the precipitated DNA fragment was isolated.

Two kinds of DNA fragments obtained as above were ligated with a DNA ligation kit (manufactured by Takara Shuzo).

Escherichia coli M15 strain was transformed with the resulting ligation solution by the above calcium chloride procedure. Colonies which had been grown on the LB agar plate containing 10 μg/ml of tetracycline were thoroughly grown in an LB medium containing 10 μg/ml of tetracycline to obtain plasmid DNA pBM 16 in accordance with the alkaline lysis method as mentioned above.

(2) Preparation of Recombinant Plasmid Having Biotin Operon

Escherichia coli DRK-332 [pKHN 31] (FERM BP-2114: FERM P-8586) containing recombinant plasmid prepared by inserting biotin operon disclosed in Japanese Unexamined Patent Publication (Kokai) No. 62-155081 into vector DNA was thoroughly grown in an LB medium containing 50 μg/ml of ampicillin, and plasmid DNA pKHN 31 was isolated by the alkali lysis method as mentioned above.

The resulting plasmid DNA pKHN 31 (1 μg) was cleaved with restriction endonuclease Hind III, subjected to a heat treatment at 65° C. for 10 minutes, and recovered by ethanol precipitation The resulting DNA fragment was added to Escherichia coli DNA polymerase buffer (500 mM tris hydrochloride, pH 7.5, 67 mM $MgCl_2$, 10 mM mercaptoethanol), and then, dCTP, dATP, dTTP and dGTP (500 μM, respectively) and DNA polymerase Klenow fragments were added. The whole was reacted at 37° C. for 30 minutes. The reaction was terminated by heating at 65° C. for 10 minutes, and DNA was recovered by ethanol precipitation. Then 5'-phosphated Xba I linker (obtained from Pharmacia) was ligated to a terminal of the resulting DNA fragment by the DNA ligation kit (manufactured by Takara Shuzo), and the resulting DNA was recovered by ethanol precipitation. The resulting DNA was cleaved with restriction endonuclease Xba I, treated by 1% agarose gel electrophoresis through low-gelling temperature agarose, stained with ethidium bromide, and then a DNA fragment (about 6.0 kb) was isolated as mentioned above.

On the other hand, vector DNA pBM 16 (1 μg) was cleaved with restriction endonuclease Xba I, subjected to heat treatment at 65° C. for 10 minutes, and recovered by ethanol precipitation.

Two kinds of DNA fragments obtained as above were ligated by a DNA ligation kit (manufactured by Takara Shuzo). With the resulting ligation solution, biotin auxotrophy strain Escherichia coli BR-4 [which had been mutagenically derived from Escherichia coli JA 221 (rec A, hsd M, hsd R, lcu B trp ΔE, lac Y) disclosed in Japanese Unexamined Patent Publication (Kokai) No. 62-155081] was transformed. The colonies which had been grown on a biotin-free minimum agar plate (0.5% of glucose, 0.4% of ammonium sulfate, 0.2% of potassium dihydrogenphosphate, 0.01% of dipotassium hydrogenphosphate, 0.4% of casamino acid free from vitamin, 15% of agar) were thoroughly grown in an LB medium containing 10 μg/ml of tetracycline, and plasmid DNA pXBA 312 was obtained by the above alkali lysis method.

(3) Transformation of Escherichia coli AD Mutant Strain with Recombinant Plasmid Containing Biotin Operon Escherichia coli DRK-3323 was transformed with recombinant plasmid pXBA 312 obtained as above in accordance with the above calcium chloride procedure. Colonies emerging on an LB agar plate containing 10 μg/ml of tetracycline were isolated to obtain Escherichia coli DRK-3323 [pXBA 312 ] (FERM BP-2117).

Example 4

As a pre-culture, the strains listed in Table 3 were inoculated with one application through a platinum loop from a maintenance agar plate culture to an L medium (10 g/l of peptone, 5 g/l of yeast extract, 1 g/l glucose, 5 g/l of sodium chloride; adjusted to pH 7.0; in the case of strains containing the recombinant plasmids, further containing 20 μg/ml of tetracycline), and cultivated at 37° C. for 8–12 hours. 50 ml of the resulting pre-culture was charged into a minijar fermenter (Marubishi Bioengineering Co., Ltd., MD-300, 5 l) containing 1700 ml of medium A having the composition as mentioned below and a main cultivation was carried out at 37° C. The pH value was adjusted to 7 with 12% aqueous ammonia, using a pH controller. The addition of the aqueous ammonia was also performed as a supply of inorganic nitrogen source. The concentration of dissolved oxygen was measured in the culture broth with a dissolved oxygen electrode, and was adjusted by mixing pure oxygen with air for aeration so that it did not drop to 3 ppm or less. The agitation was 500 rpm, and the aeration amount was 1 v.v.m. Because a phenomenon occurs whereby the concentration of the dissolved oxygen is suddenly increased when a concentration of glucose in the culture broth is around zero, the concentration of glucose in the culture broth was maintained at 1–5g/l, using the above phenomenon as an indicator, by feeding the glucose solution A having the following composition. The results of a 24 hour cultivation are shown in Table 3.

| Medium A | (g/l) |
| --- | --- |
| Disodium phosphate (12$H_2O$) | 17.6 |
| Potassium phosphate | 2.4 |
| Ammonium sulfate | 1.0 |
| Yeast extract | 10.0 |
| Peptone | 10.0 |
| Ferrous sulfate (7$H_2O$) | 0.1 |
| Calcium chloride (2$H_2O$) | 0.05 |
| Manganese chloride (4$H_2O$) | 0.05 |
| Magnesium sulfate (7$H_2O$) | 0.1 |
| Glucose | 5.0 |
| Feeding Glucose Solution A | |
| Glucose | 750.0 |
| Magnesium sulfate (7$H_2O$) | 5.0 |

TABLE 3

| Strain | Escherichia coli DRK-332 (FERM BP-2113) | Escherichia coli DRK-332 [pXBA312] | Escherichia coli DRK-3323 (FERM BP-2116) | Escherichia coli DRK-3323 [pXBA312] (FERM BP-2117) |
|---|---|---|---|---|
| Cell conc. (g/l) | 31 | 25 | 73 | 62 |
| Amount of accumulated acetate (g/l) | 16 | 15 | 5 | 4 |
| Amount of accumulated acetate per bacterial dry weight | 0.52 | 0.6 | 0.07 | 0.06 |
| Amount of accumulated desthiobiotin (mg/l) | 2 | 23 | 2 | 10 |
| Yield of biotin (mg/l) | 2 | 21 | 5 | 52 |

Example 5

As a pre-culture, the strains listed in Table 4 were inoculated with one application through a platinum loop from a maintenance agar plate culture to an L medium (10 g/l of peptone, 5 g/l of yeast extract, 1 g/l of glucose, 5 g/l of sodium chloride, 20 mg/ml of tetracycline; adjusted to pH 7.0), and cultivated at 37° C. for 8–12 hours. Then 50 ml of the resulting pre-culture was charged into a minijar fermenter (Marubishi Bioengineering Co., Ltd., MD-300, 5 l) containing 1700 ml of medium B having the composition as mentioned below and a main cultivation was carried out at 37° C. The pH value was adjusted to 7 with 12% aqueous ammonia, using a pH controller. The concentration of dissolved oxygen was adjusted by mixing pure oxygen with air for aeration so that it did not drop to 3 ppm or less. The agitation was 500 rpm, and the aeration amount was 1 v.v.m. Because a phenomenon occurs whereby the concentration of the dissolved oxygen is suddenly increased when a concentration of glucose in the culture broth is around zero, the concentration of glucose in the culture broth was maintained at 1–5 g/l, using the above phenomenon as an indicator, by feeding the glucose solution B having the following composition. The results of a 24 hour cultivation are shown in Table 4. For biotin and dethiobiotin in the culture broth, quantitative analyses were carried out by a bioassay using *Lactobacillus plantarum* (ATCC 8014) and *Saccharomyces cerevisiae* (ATCC 7754), and colorimetry using avidin (Methods in Enzymology, vol. XVIII, p. 419). Table 4 shows that, in the case of the strain DRK-332 [pXBA 312 ] which was transformed from the parent strain DRK-332 with the plasmid pXBA 312, acetate was accumulated in a considerable amount, the cell concentration was low, the yield of biotin was 40 mg/l, and the intermediate, desthiobiotin was accumulated in an amount of 83 mg/l, whereas in the case of the strain DRK-3323 [pXBA 312 ] according to the present invention, the amount of accumulated acetate was as low as 6 g/l, the cell concentration was 65 g/l, desthiobiotin was efficiently metabolized to biotin, and the yield of biotin reached 105 mg/l.

| Medium B | (g/l) |
|---|---|
| Disodium phosphate (12H$_2$O) | 17.6 |
| Potassium phosphate | 2.4 |
| Ammonium sulfate | 1.0 |
| Yeast extract | 10.0 |
| Peptone | 10.0 |
| dl-Alanine | 3.0 |
| Ferrous sulfate (7H$_2$O) | 0.1 |
| Calcium chloride (2H$_2$O) | 0.05 |
| Manganese chloride (4H$_2$O) | 0.05 |
| Magnesium sulfate (7H$_2$O) | 0.1 |
| Glucose | 5.0 |
| Feeding Glucose Solution B | |
| Glucose | 750.0 |
| Magnesium Sulfate (7H$_2$O) | 5.0 |
| dl-Alanine | 7.0 |

TABLE 4

| Strain | Escherichia coli DRK-332 [pXBA312] | Escherichia coli DRK-3323 [pXBA312] (FERM BP-2117) |
|---|---|---|
| Cell conc. (g/l) | 27 | 65 |
| Amount of accumulated acetate (g/l) | 17 | 6 |
| Amount of accumulated acetate per bacterial dry weight | 0.63 | 0.09 |
| Amount of accumulated desthiobiotin (mg/l) | 83 | 15 |
| Yield of biotin (mg/l) | 40 | 105 |

Example 6

Preparation of AD Mutant Strain Containing Recombinant Plasmid Having hCT-lac'z Fused Gene

*Escherichia coli* M15 [pZT 32] (FERM BP-2115) containing recombinant plasmid having a gene coding fusion protein (hCT-peptide containing collagenase cleavage site-β-galactosidase) [disclosed in Japanese Unexamined Patent Publication (Kokai) No. 63-226288], and tac promoter obtained from plasmid pKK 223-3 (manufactured by Pharmacia) as an expression promoter was thoroughly grown in an LB medium containing 50 μg/ml of ampicillin, and a plasmid DNA pZT 32 was isolated in accordance with the alkaline lysis method as mentioned above. *Escherichia coli* NA 75 was transformed with the resulting plasmid DNA pZT 32 in accordance with the above calcium chloride procedure. Colonies which had been grown on an LB agar plate containing 50 μg/ml of ampicillin were isolated to obtain *Escherichia coli* NA 75 [pZT 32].

Example 7

As a pre-culture, the strains listed in Table 5 were inoculated with one application through a platinum loop from a maintenance agar plate culture to an L medium (10 g/l of peptone, 5 g/l of yeast extract, 1 g/l of glucose, 5 g/l of sodium chloride, 50 mg/l of ampicillin; adjusted to pH 7.0) and cultivated at 37° C. for 8–12 hours. Then 50 ml of the resulting pre-culture was charged into a minijar fermenter (Marubishi Bioengineering Co., Ltd., MD-300, 5 l) containing 1700 ml of the medium A as mentioned above and a main cultivation was carried out at 37° C. The pH value was adjusted to 7 with 12% aqueous ammonia, using a pH controller. The concentration of dissolved oxygen was adjusted by mixing pure oxygen with air for aeration so that it did not drop to 3 ppm or less. The agitation was 500 rpm, and the aeration amount was 1 v.v.m. Because a phenomenon occurs whereby the concentration of the dissolved oxygen is suddenly increased when a concentration of glucose in the culture broth is around zero, the concentration of glucose in the culture broth was maintained at 1–5 g/l, using the above phenomenon as an indicator by feeding the above glucose solution A. When, in the course of the cultivation, the amount of accumulated acetate in the culture broth became 3–4 g/l, and thus the growth activity of bacterial cells began dropping, the hCT-lac'z fused gene was expressed by adding 0.25 g/l of isopropyl-β-D-thiogalactopyranoside (IPTG). IPTG was added 9 hours after the start of the cultivation of *Escherichia coli* M15 [pZT 32] strain, or 14 hours for the *Escherichia coli* NA 75 [pZT 32] strain. The cultivation was further continued and completed 24 hours later. Bacterial cells were recovered from the culture broth by centrifugation, washed with sterilized water, suspended in 10 mM tris hydrochloride (pH 8.0)—1 mM EDTA—0.1 mM DTT, and broken by an X-press (manufactured by AB BIOX). The supernant was obtained by centrifugation and used as a cell extract.

For the cell extract, quantitative analysis tests were carried out as follows:

(1) Determination of Human Calcitonin

Determination was performed by radioimmunoassay, using calcitonin kit "Dai ichi" (manufactured by Dai ichi Radioisotope Laboratories). The test procedure was performed in accordance to instructions given for the kit.

(2) Determination of β-Galactosidase

The enzyme was determined in accordance with the Miller method (Miller, J. H., Exp. Mol. Gen. Cold Spring Harbor Lab. Press Cold Spring Harbor, N.Y. p352, 1972), using o-nitrophenylgalactopyranoside (ONPG) as a substrate. The enzymatic activity necessary to degrade 1 nmole of ONPG at 28° C. for 1 minute was designated as 1 unit.

(3) Determination of Protein

The Lowry method (Lowry, O. H., J. Riol. Chem., 193, 265, 1951) was used, and standard curve was prepared by using bovine serum albumin (manufactured by Sigma, Fraction V).

The results are shown in Table 5.

TABLE 5

| Strain | M15 [pZT32] (FERM BP-2115) | NA-75 [pZT32] |
|---|---|---|
| Cell conc. (g/l) | 19 | 56 |
| Amount of accumulated acetate (g/l) | 13.0 | 5.4 |

TABLE 5-continued

| Strain | | M15 [pZT32] (FERM BP-2115) | NA-75 [pZT32] |
|---|---|---|---|
| Amount of accumulated acetate per bacterial dry weight | | 0.68 | 0.10 |
| Cell extract | Calcitonin (mg/l) | 57 | 185 |
| | β-Galactosidase (U/mg protein) | 60.000 | 68.000 |

The fusion protein (hCT-peptide containing collagenase cleavage site-β-galactosidase) produced and accumulated was purified in accordance with a conventional method for purifying a protein, using the activity of β-galactosidase as an indicator, and cleaved with collagenase by the method disclosed in Japanese Unexamined Patent Publication (Kokai) No. 63-226288. hCT having C-terminal glycine was separated by HPLC. hCT having C-terminal glycine may be easily converted to hCT through the reaction with C-terminal amidation enzyme (Bradury, A. F. et al, Nature, 298, 686, 1982). The converted hCT can be efficiently used as medicine.

INDUSTRIAL APPLICABILITY

The novel microorganism according to the present invention exhibits a low acetate forming capability which is at most one fifth that of the wild type, and thus the growth of the bacterial cells is not easily inhibited with acetate, the cells can be easily cultivated to a high density, and therefore, a useful substance is obtained at a considerably high yield. When biotin is produced by using the microorganism according to the present invention in fermentation, the yield thereof is significantly enhanced in comparison with the prior art. In addition, the yield can be further increased by cultivation in a medium containing alanine.

Although the present invention has been described with reference to specific embodiments, various changes and modifications obvious to those skilled in the art are deemed to be within the spirit, scope and concept of the invention.

Reference to Deposited Microorganisms

International Depository Authority: Fermentation Research Institute, Agency of Industrial Science and Technology Address: 1-3 Higashi 1 chome, Tsukuba-shi, Ibaraki-ken, 305, Japan Deposition Number and Date:

1. FERM BP-2105: Oct. 17, 1988
2. FERM BP-2113: Dec. 26, 1985 (transferred from FERM P-8585 deposited on Dec. 26, 1985)
3. FERM BP-2114: Dec. 26, 1985 (transferred from FERM P-8586 deposited on Dec. 26, 1985)
4. FERM BP-2115: Mar. 12, 1987 (transferred from FERM P-9266 deposited on Mar. 12, 1987)
5. FERM BP-2116: Oct. 28, 1987 (transferred from FERM P-9675 deposited on Oct. 28, 1987)
6. FERM BP-2117: Oct. 28, 1987 (transferred from FERM P-9676 deposited on Oct. 28, 1987).

What is claimed is:

1. A process for producing biotin, desthiobiotin, or a combination thereof, comprising the steps of cultivating to a high density an *Escherichia coli* strain (i) having an ability to form acetate of at most one fifth the amount produced by an isogenic strain of *Escherichia* coli and (ii) containing a recombinant plasmid comprising a biotin operon, said strain converting a greater percentage of desthiobiotin to biotin than an isogenic strain of *Escherichia coli*; and recovering biotin, desthiobiotin, or both.

2. A process according to claim 1, wherein, in the *Escherichia coli* strain, feedback repression by biotin is removed.

3. A process according to claim 2, wherein the *Escherichia coli* strain is cultivated in a medium containing 1 to 10 g/l of alanine.

4. A process as claimed in claim 1, wherein said cultivated *Escherichia coli* strain is obtained by transforming an *Escherichia coli* strain of deposit no. FERM BP-2116 with said recombinant plasmid.

5. A process for producing biotin, desthiobiotin, or a combination thereof comprising culturing *Escherichia coli* strain DRK-3323 transformed with plasmid pXBA312, deposit no. FERM BP-2117, wherein said strain has the ability to form acetate of at most one fifth the amount produced by isogenic *Escherichia coli* strain DRK-332, wherein the feedback repression by biotin is removed in both strain DRK-3323 and in strain DRX-332, and wherein plasmid pXBA312 comprises the biotin operon, and recovering biotin, desthiobiotin, or both.

* * * * *

UNITED STATES PATENT AND TRADEMARK OFFICE
CERTIFICATE OF CORRECTION

PATENT NO. : 5,919,662
DATED : July 6, 1999
INVENTOR(S) : Shinichiro HAZE, et al.

It is certified that error appears in the above-identified patent and that said Letters Patent is hereby corrected as shown below:

Title page,
Related U.S. Application Data [62], contains a typographical error wherein "Nov. 7, 1987, abandoned." should read --Nov. 7, 1988--.

Signed and Sealed this

Eighth Day of February, 2000

Attest:

Q. TODD DICKINSON

Attesting Officer

Commissioner of Patents and Trademarks